(12) United States Patent
Engelhard

(10) Patent No.: US 9,408,937 B2
(45) Date of Patent: Aug. 9, 2016

(54) PHOTO-CATALYZING FLUID MOBILIZING SYSTEM AND METHOD

(71) Applicant: Rolf Engelhard, Prescott, AZ (US)

(72) Inventor: Rolf Engelhard, Prescott, AZ (US)

( * ) Notice: Subject to any disclaimer, the term of this patent is extended or adjusted under 35 U.S.C. 154(b) by 0 days.

(21) Appl. No.: 14/887,235

(22) Filed: Oct. 19, 2015

(65) Prior Publication Data

US 2016/0038625 A1 Feb. 11, 2016

Related U.S. Application Data

(63) Continuation of application No. 13/076,367, filed on Mar. 30, 2011, now Pat. No. 9,162,903.

(60) Provisional application No. 61/319,215, filed on Mar. 30, 2010.

(51) Int. Cl.
| | | |
|---|---|---|
| C02F 1/32 | (2006.01) | |
| A61L 9/20 | (2006.01) | |
| B01D 53/88 | (2006.01) | |
| B01J 19/12 | (2006.01) | |
| B01J 19/18 | (2006.01) | |
| C02F 1/72 | (2006.01) | |

(52) U.S. Cl.
CPC ............... *A61L 9/205* (2013.01); *B01D 53/885* (2013.01); *B01J 19/123* (2013.01); *B01J 19/18* (2013.01); *C02F 1/32* (2013.01); *C02F 1/325* (2013.01); *C02F 1/725* (2013.01); *B01D 2255/20707* (2013.01); *B01D 2255/802* (2013.01); *B01D 2257/708* (2013.01); *B01D 2257/91* (2013.01); *B01D 2259/4508* (2013.01); *B01D 2259/4533* (2013.01); *B01D 2259/804* (2013.01); *B01J 2219/0877* (2013.01); *B01J 2219/0892* (2013.01); *C02F 2201/326* (2013.01); *C02F 2201/3227* (2013.01); *C02F 2201/3228* (2013.01); *C02F 2305/10* (2013.01); *Y02W 10/37* (2015.05)

(58) Field of Classification Search
CPC .................................... C02F 1/32; B01J 19/08
See application file for complete search history.

(56) References Cited

U.S. PATENT DOCUMENTS

| | | |
|---|---|---|
| D48,392 S | 1/1916 | Loheide |
| 2,255,491 A | 9/1941 | Mohen |
| 2,738,224 A | 3/1956 | Checkovich et al. |
| 4,422,824 A | 12/1983 | Eisenhardt, Jr. |
| 5,680,016 A | 10/1997 | Valcke |
| D398,044 S | 9/1998 | Gutmann |
| 5,833,740 A | 11/1998 | Brais |

(Continued)

FOREIGN PATENT DOCUMENTS

| | | | |
|---|---|---|---|
| CN | 002531297 Y | * 1/2003 | ............... F24F 3/16 |
| CN | 2664666 Y | 12/2004 | |

(Continued)

*Primary Examiner* — Walter D Griffin
*Assistant Examiner* — Cameron J Allen
(74) *Attorney, Agent, or Firm* — Mintz Levin Cohn Ferris Glovsky and Popeo, P.C.

(57) ABSTRACT

A photo-catalyzing fluid mobilizing system and method are disclosed. A chamber has a power source. A fluid mobilizer is mounted in the chamber and connected with the power source to mobilize a fluid through the chamber. The fluid mobilizer includes one or more fan blades that are coated with a photo catalyst. A UV light source is mounted in the chamber proximate the fluid mobilizer and connected with the power source to catalyze the photo catalyst coating the blades to purifier the fluid being mobilized thereover.

12 Claims, 3 Drawing Sheets

(56) References Cited

U.S. PATENT DOCUMENTS

| | | | |
|---|---|---|---|
| 6,063,343 A | 5/2000 | Say et al. | |
| D433,494 S | 11/2000 | Pinchuk et al. | |
| 6,303,087 B1 * | 10/2001 | Wedekamp | C02F 1/325 210/748.11 |
| 6,365,113 B1 * | 4/2002 | Roberts | A61L 2/10 422/186.3 |
| D461,004 S | 7/2002 | Searle | |
| D491,654 S | 6/2004 | Gatchell et al. | |
| D495,043 S | 8/2004 | Gatchell et al. | |
| D496,096 S | 9/2004 | Wang et al. | |
| D501,248 S | 1/2005 | Chi-Hsiang et al. | |
| 6,939,397 B2 | 9/2005 | Nelsen et al. | |
| D513,797 S | 1/2006 | Wang | |
| D522,116 S | 5/2006 | Zhixiang | |
| D539,406 S | 3/2007 | Wang | |
| D540,453 S | 4/2007 | Wang | |
| D545,951 S | 7/2007 | Bucher et al. | |
| D574,475 S | 8/2008 | Spiegel | |
| D582,024 S | 12/2008 | Gao | |
| D586,899 S | 2/2009 | Searle | |
| D588,686 S | 3/2009 | Spiegel | |
| D594,947 S | 6/2009 | Lewis | |
| D603,949 S | 11/2009 | Campbell et al. | |
| 7,695,675 B2 * | 4/2010 | Kaiser | A23L 3/28 210/319 |
| D638,923 S | 5/2011 | Choi | |
| D639,919 S | 6/2011 | Yu | |
| 7,972,564 B2 * | 7/2011 | Chan | A61L 2/10 204/157.3 |
| 8,017,073 B2 | 9/2011 | Engelhard | |
| D658,752 S | 5/2012 | Farone | |
| 8,277,735 B2 | 10/2012 | Engelhard | |
| D675,303 S | 1/2013 | Raupach et al. | |
| D678,493 S | 3/2013 | Lacotta et al. | |
| D678,992 S | 3/2013 | Choi | |
| D683,006 S | 5/2013 | Spiegel | |
| D683,007 S | 5/2013 | Spiegel | |
| D691,255 S | 10/2013 | Abbondanzio et al. | |
| D703,804 S | 4/2014 | Nuzzi, Jr. | |
| D705,410 S | 5/2014 | Terao | |
| 8,734,724 B2 | 5/2014 | Engelhard | |
| D714,923 S | 10/2014 | Engelhard et al. | |
| D731,633 S | 6/2015 | Farone et al. | |
| 2002/0098127 A1 | 7/2002 | Bollini | |
| 2003/0230477 A1 | 12/2003 | Fink et al. | |
| 2006/0057020 A1 | 3/2006 | Tufo | |
| 2007/0207722 A1 | 9/2007 | McLeod | |
| 2008/0014111 A1 | 1/2008 | Hedman | |
| 2008/0048541 A1 | 2/2008 | Sumrall et al. | |
| 2008/0112845 A1 | 5/2008 | Dunn et al. | |
| 2008/0213129 A1 | 9/2008 | van der Pol et al. | |
| 2009/0066257 A1 | 3/2009 | Kominami et al. | |
| 2009/0285727 A1 | 11/2009 | Levy | |
| 2010/0143205 A1 | 6/2010 | Engelhard | |

FOREIGN PATENT DOCUMENTS

| | | |
|---|---|---|
| EP | 1600201 A1 | 11/2005 |
| JP | 2002-174444 A | 6/2002 |
| JP | 2002-178745 A | 6/2002 |
| JP | 2004-036912 A | 2/2004 |
| JP | 2004-069129 A | 3/2004 |
| JP | 2005-161022 A | 6/2005 |
| JP | 2005-164069 A | 6/2005 |
| JP | 003110098 | 6/2005 |
| JP | 2008-116139 A | 5/2008 |
| JP | 2009-538410 A | 11/2009 |
| WO | WO-2007/142907 A1 | 12/2007 |
| WO | WO-2008/117962 A1 | 10/2008 |

* cited by examiner

PHOTO-CATALYZING FLUID MOBILIZING SYSTEM AND METHOD

CROSS REFERENCE TO RELATED APPLICATIONS

This application is a continuation application of U.S. patent application Ser. No. 13/076,367, filed Mar. 30, 2011, titled "PHOTO-CATALYZING FLUID MOBILIZING SYSTEM AND METHOD," which in turn claims the benefit of priority under 35 U.S.C. §119 to U.S. Provisional Patent Application Ser. No. 61/319,215, filed on Mar. 30, 2010, entitled, "PHOTO-CATALYZING FLUID MOBILIZING SYSTEM AND METHOD", the entire disclosures of which is incorporated by reference herein.

BACKGROUND

One of the most effective methods for air purification is photo catalysis. Photo catalysis occurs when a photo catalyst is irradiated by ultra-violet light in the UV-A, UV-B and UV-C range. In a typical application, a UV-irradiated surface is coated with a photo catalytic material such as titanium dioxide. Photo catalysis occurs on a very thin boundary layer above the surface of the photo catalyst. This presents one of the limitations of photo catalysis for air or water purification, since it is difficult to bring all the fluid to be purified to the UV-irradiated photo catalyst. This invention addresses this limitation and presents a novel method to move a fluid past an irradiated photo catalyst.

Photo-catalysis is generally defined as "acceleration by the presence of a catalyst". A catalyst does not change in itself or being consumed in the chemical reaction. This definition includes photosensitization, a process by which a photochemical alteration occurs in one molecular entity as a result of initial absorption of radiation by another molecular entity called the photosensitized. Chlorophyll of plants is a type of photo catalyst. Compared to photosynthesis, in which chlorophyll captures sunlight to turn water and carbon dioxide into oxygen and glucose, photo catalysis with light and water creates a strong oxidation agent to break down any organic matter to carbon dioxide and water.

Photo catalysis is effective for sterilizing, deodorizing, and purifying fluids such as air or water. However, conventional fluid purification systems do not take advantage of photo catalysts.

SUMMARY

This document presents a system and method for photo-catalyzing and mobilizing a fluid, such as air or water.

According to one aspect, a photo-catalyzing fluid mobilizing system includes a chamber having a power source, and a fluid mobilizer mounted in the chamber and connected with the power source. The fluid mobilizer mobilizes a fluid through the chamber using one or more fan blades that are coated with a photo catalyst. The system further includes a UV light source mounted in the chamber proximate the fluid mobilizer and connected with the power source to catalyze the photo catalyst coating the blades to purifier the fluid being mobilized thereover.

According to another aspect, a photo-catalyzing fluid mobilizing method includes the steps of mobilizing, using a fluid mobilizer, a fluid through a chamber and over at least one fan blade of the fluid mobilizer, the fan blade being coated with a photo catalyst. The method further includes the steps of irradiating the fan blade with UV light to catalyze the photo catalyst, and purifying the fluid being mobilized through the chamber with the catalyzed photo catalyst.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1:
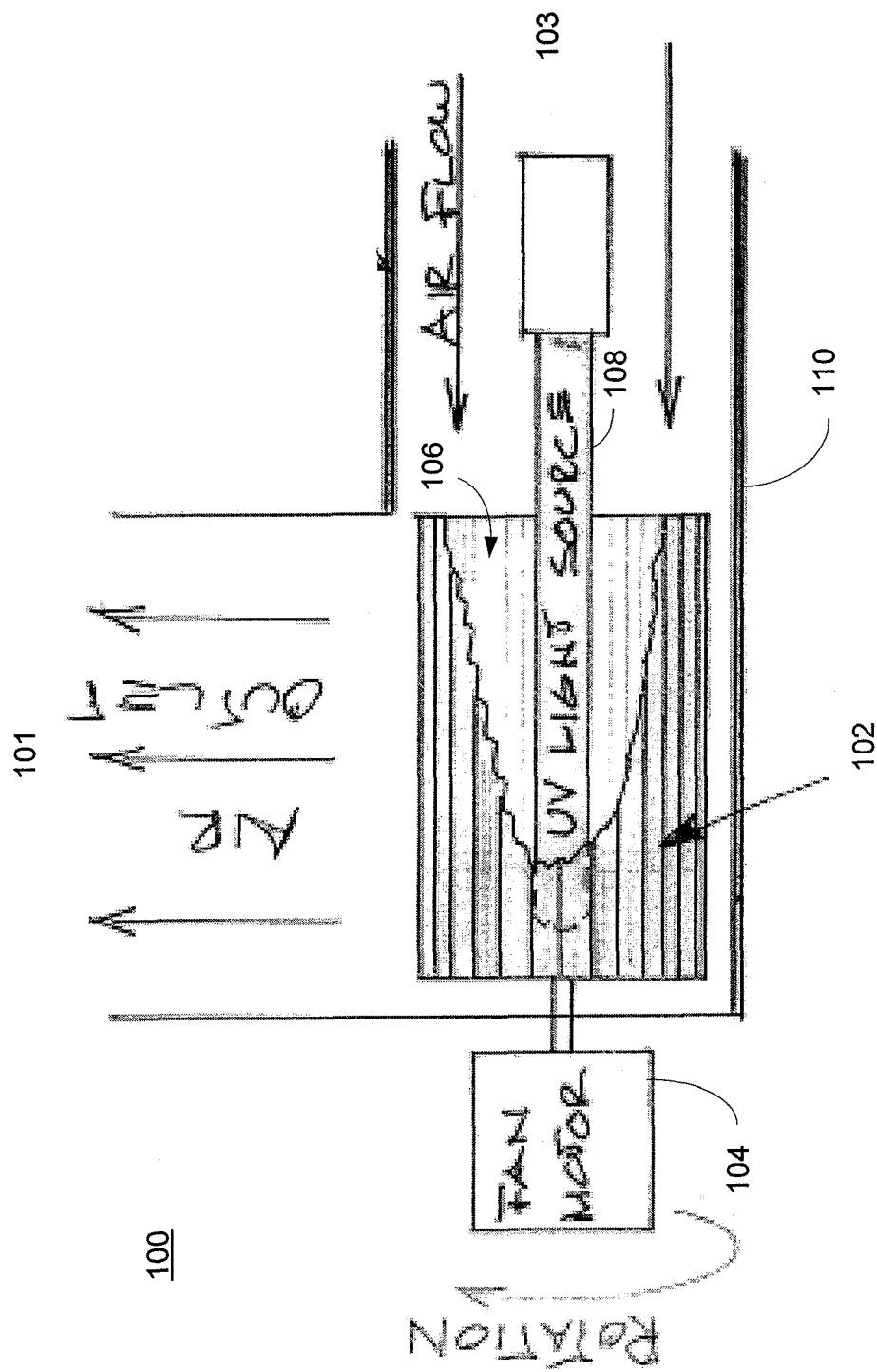
FIG. 1 is a photo-catalyst fluid purification system using a centrifugal or radial fan having a photo-catalytic coating.

This document describes a high intensity air purifier, a super oxidation purifier, and a controller for controlling operation of any of various purification systems described herein.

When a photo catalyst such as titanium dioxide ($T_1O_2$) absorbs Ultraviolet (UV) radiation from sunlight or other illuminated light source (fluorescent lamps), it will produce pairs of electrons and holes. The electron of the valence band of titanium dioxide becomes excited when illuminated by light. The excess energy of this excited electron promoted the electron to the conduction band of titanium dioxide therefore creating the negative-electron (e−) and positive-hole (h+) pair. This stage is referred as the semiconductor's 'photo-excitation' state. The energy difference between the valence band and conduction band is known as the "Band Gap." Wavelength of the light necessary for photo-excitation is: 1240 (Planck's constant, h)/3.2 ev (band gap energy)=388 nm.

For sterilization, a photo catalyst not only kills bacteria cells, but also decomposes the cell itself. A titanium dioxide photo catalyst has been found to be more effective than any other antibacterial agent, because the photo catalytic reaction works even when there are cells covering the surface and while the bacteria are actively propagating. The end toxin produced at the death of cell is also expected to be decomposed by the photo catalytic action. Titanium dioxide does not deteriorate and it shows a long-term anti-bacterial effect. Generally speaking, disinfections by titanium oxide are three times stronger than chlorine, and 1.5 times stronger than ozone.

On the deodorizing application, the hydroxyl radicals accelerate the breakdown of any Volatile Organic Compounds or VOCs by destroying the molecular bonds. This will help combine the organic gases to form a single molecule that is not harmful to humans thus enhance the air cleaning efficiency. Some of the examples of odor molecules are: tobacco odor, formaldehyde, nitrogen dioxide, urine and fecal odor, gasoline, and many other hydrocarbon molecules in the atmosphere. An air purifier with $T_1O_2$ can prevent smoke and soil, pollen, bacteria, virus and harmful gas as well as seize the free bacteria in the air by filtering percentage of 99.9% with the help of the highly oxidizing effect of photo catalyst.

For air purification, the photo catalytic reactivity of titanium oxides can be applied for the reduction or elimination of polluted compounds in air such as NOx, cigarette smoke, as well as volatile compounds arising from various construction materials. Also, high photo catalytic reactivity can be applied to protect lamp-houses and walls in tunneling, as well as to prevent white tents from becoming sooty and dark. Atmospheric constituents such as chlorofluorocarbons (CFCs) and CFC substitutes, greenhouses gases, and nitrogenous and sulfurous compounds undergo photochemical reactions either directly or indirectly in the presence of sunlight. In a polluted area, these pollutants can eventually be removed.

For water purification, a photo catalyst coupled with UV lights can oxidize organic pollutants into nontoxic materials, such as CO2 and water, and can disinfect certain bacteria. This technology is very effective at removing further hazardous organic compounds (TOCs) and at killing a variety of bacteria and some viruses in the secondary wastewater treatment. Photo catalytic detoxification systems have been demonstrated to effectively kill fecal coli form bacteria in secondary wastewater treatment.

With reference to FIG. 1, a photo-catalytic fan 100 includes an inlet 101, an outlet 103, and an air fan/blower that has a fluid mobilizer 102, which can be a rotor, blower wheel, fan, propeller or impeller, to mobilize a fluid such as air or water. The fluid mobilizer 102 can be operated by a fan motor 104. The fluid mobilizer 102 is coated with a photo catalyst 106, which can be any material that produces a photo catalytic reaction when irradiated by ultra-violet (UV) light. One such photo catalyst is titanium dioxide. The fluid mobilizer serves several different functions: it moves the fluid that is to be purified; and it acts as the substrate for the photo catalytic material. Fans, rotor blades, impellers characteristically have a large surface area, which makes them ideally suited as the substrate for the photo catalyst.

The photo-catalytic fan 100 further includes an ultra-violet light source 108 that irradiates the photo catalytic surfaces of the fan/blower blades of the fluid mobilizer 102. The ultra-violet light source 108 can be one or more ultra-violet lamps, which can be constructed in many different shapes including bulb-shaped, cylindrical, u-shaped, circular and spot lamps such as recently developed LEDs or UV lasers. As such, lamp shapes can be chosen for each different type of fluid mobilizer 102, to ideally irradiate the maximum surface area of the photo catalyst 106.

Figure 2:
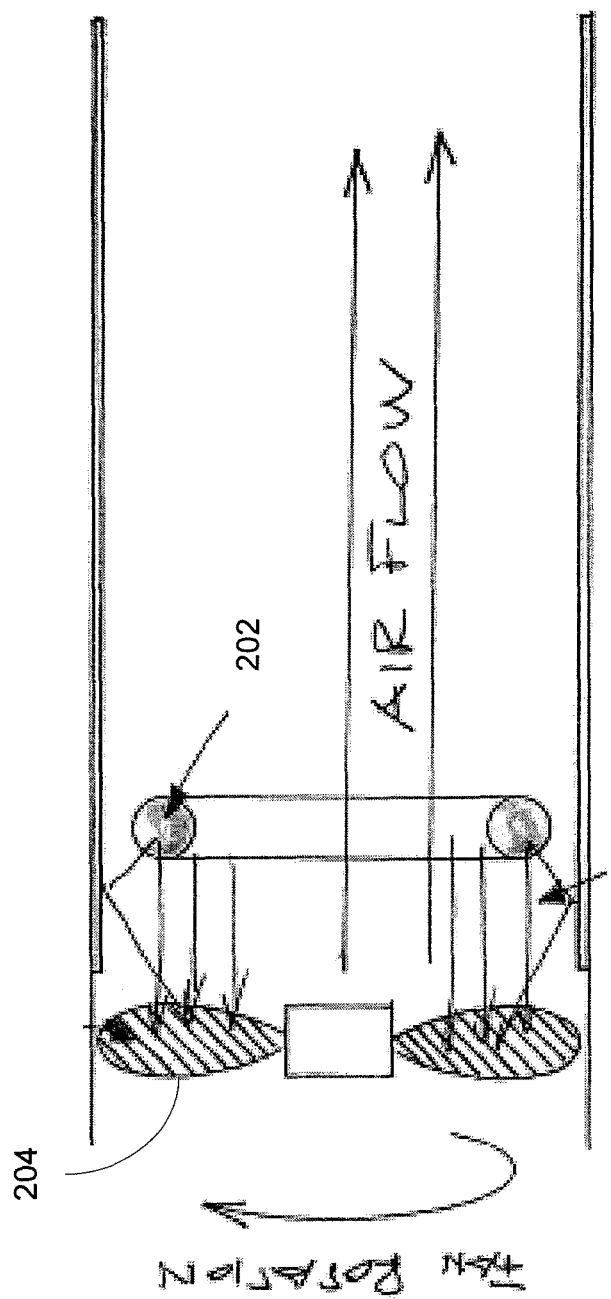
FIG. 2 is a photo-catalyst fluid purification system using a propeller or impeller-type fan having a photo-catalytic coating.
Figure 3:
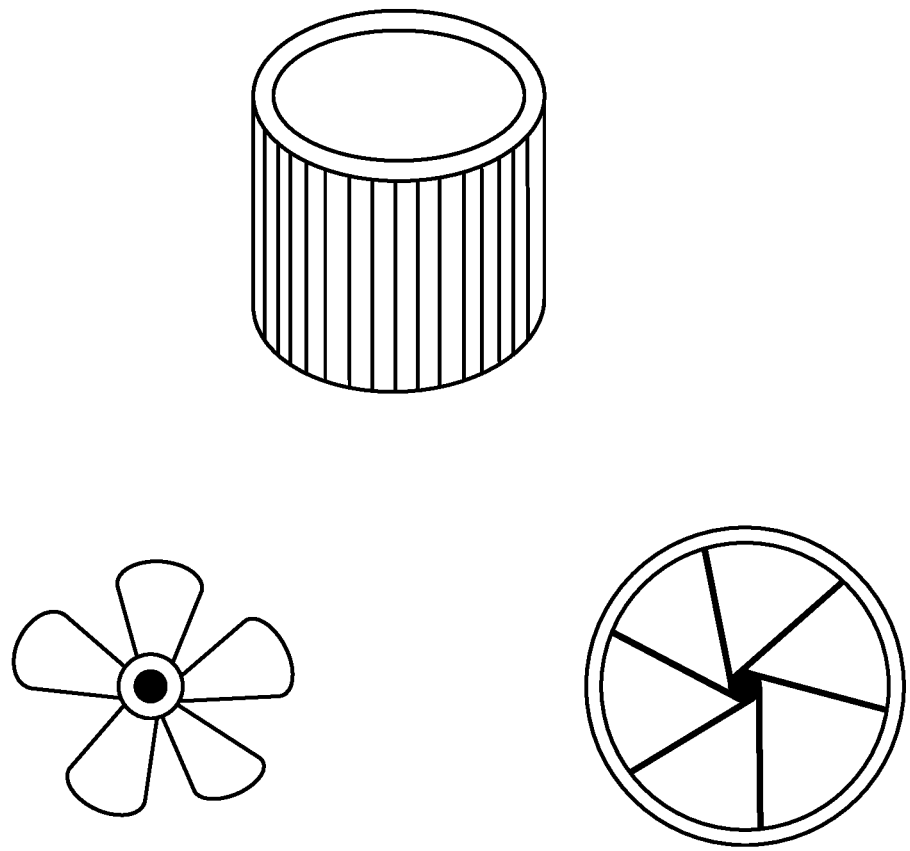
FIG. 3 illustrates alternative fan configurations for a fluid mobilizer.

FIGS. 2 and 3, along with FIG. 1, show a number of possible fan/lamp combinations. FIG. 2 shows a circular ultra-violet lamp 202 that provides the ultra-violet light source, and where a fan blade 204 is coated with a photo catalyst. In one preferred implementation, the ultra-violet lamp 202 is ring-shaped and circumscribes an inner surface of the chamber that contains the ultra-violet lamp 202. FIG. 3 illustrates alternative fan configurations for a fluid mobilizer.

The photo-catalytic fan 100 further includes a chamber 110 that contains the fluid mobilizer 102 and the ultra-violet light source 108. The chamber may include a UV-reflective surface on the interior walls of the part of the chamber that houses the fan/blower and the UV light source 108. The reflective surface is preferably be a lambertian reflector that reflects a very high percentage of the UV light that strikes the interior wall of the chamber 110, and directs this light toward the photo catalytic surfaces of the fan/blower blades of the fluid mobilizer 102.

The photo-catalytic fan 100 is suitable for any types of fluids, including air or water. In a water purification device, the shape of the propeller, impeller, rotor or fan blades will have a different shape or pitch than the air blades and will rotate at a speed that is appropriate to move or mobilize water. The strength of the UV light source is also adjustable so as to adjust for the reflective and refractive qualities of water. In some implementations, a single device can be made for both water and air, and include a setting for either mode. The setting will adjust the shape or pitch of the fan blades, rotation speed of the fan, and possibly the light strength of the UV light source.

The photo-catalytic fan 100 can further include filters or flow directors within the chamber, for filtering out large particles and to direct the air properly toward the UV light source, respectively. The chamber can be a hollow cylinder, and can be made of any suitable rigid material, such as plastic, nylon, stainless steel, aluminum, or the like.

Although a few embodiments have been described in detail above, other modifications are possible. Other embodiments may be within the scope of the following claims.

The invention claimed is:

1. A method of mobilizing and photo-catalyzing a fluid, the method comprising:
    mobilizing, using a fluid mobilizer, a fluid through a passageway formed between a UV light source and an inner surface of at least one fan blade positioned within a chamber of the fluid mobilizer, the at least one fan blade being at least partly coated with a photo catalyst;
    irradiating the at least one fan blade with a UV light source to catalyze the photo catalyst, the UV light source being disposed within the at least one fan blade such that the at least one fan blade rotates about the UV light source and forms the passageway between the UV light source and the inner surface of the at least one fan blade; and
    purifying the fluid being mobilized through the chamber with the catalyzed photo catalyst.

2. The method in accordance with claim 1, wherein the UV light source includes a UV lamp.

3. The method in accordance with claim 2, wherein the UV lamp is ring-shaped and circumscribes an interior surface of the chamber.

4. The method in accordance with claim 1, wherein the fluid is water, and wherein a strength of the UV light source is adjustable to adapt to the reflective and refractive qualities of the water.

5. The method in accordance with claim 1, wherein an interior surface of the chamber includes a UV reflective surface.

6. The method in accordance with claim 1, wherein the fluid mobilizer comprises one or more of a rotor, a blower wheel, a fan, a propeller, and an impeller.

7. A method of moving and photo-catalyzing a fluid, the method comprising:
    moving, using a fan, a fluid through a passageway formed between a UV light source and an inner surface of at least one fan blade positioned within a chamber, the moving causing the fluid to move over at least one fan blade of the fan, the at least one fan blade being at least partly coated with a photo catalyst;
    irradiating the at least one fan blade with a UV light source to catalyze the photo catalyst, the UV light source being disposed within the at least one fan blade such that the at least one fan blade rotates about the UV light source and forms the passageway between the UV light source and the inner surface of the at least one fan blade; and
    purifying the fluid being moved through the chamber with the catalyzed photo catalyst.

8. The method in accordance with claim 7, wherein the UV light source includes a UV lamp.

9. The method in accordance with claim 8, wherein the UV lamp is ring-shaped and circumscribes an interior surface of the chamber.

10. The method in accordance with claim 7, wherein the fluid is water, and wherein a strength of the UV light source is adjustable to adapt to the reflective and refractive qualities of the water.

11. The method in accordance with claim 7, wherein an interior surface of the chamber includes a UV reflective surface.

12. A method of purifying a fluid, the method comprising:
- receiving a fluid into a chamber, the chamber having a fan and a UV light source, the UV light source disposed within at least one fan blade of the fan such that the at least one fan blade rotates about the UV light source and forms a passageway between the UV light source and the at least one fan blade, the at least one fan blade being at least partly coated with a photo catalyst;
- exposing the at least one fan blade to a UV light source to catalyze the photo catalyst on the at least one fan blade; and
- moving, using the fan, the fluid through the chamber to cause the fluid to move through the passageway and over the catalyzed photo catalyst to purify the fluid.

\* \* \* \* \*